US007289845B2

(12) United States Patent
Sweeney et al.

(10) Patent No.: US 7,289,845 B2
(45) Date of Patent: *Oct. 30, 2007

(54) CURVATURE BASED METHOD FOR SELECTING FEATURES FROM AN ELECTROPHYSIOLOGIC SIGNAL FOR PURPOSE OF COMPLEX IDENTIFICATION AND CLASSIFICATION

(75) Inventors: Robert J. Sweeney, Woodbury, MN (US); Eric G. Lovett, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/734,327

(22) Filed: Dec. 12, 2003

(65) Prior Publication Data

US 2004/0127806 A1    Jul. 1, 2004

Related U.S. Application Data

(63) Continuation of application No. 09/703,269, filed on Oct. 31, 2000, now Pat. No. 6,684,100.

(51) Int. Cl.
*A61B 5/04* (2006.01)
*A61B 5/0456* (2006.01)
*A61B 5/0472* (2006.01)

(52) U.S. Cl. ........................... 600/517; 600/515
(58) Field of Classification Search ............... 600/508, 600/513, 514, 515, 516, 517, 522
See application file for complete search history.

(56) References Cited

U.S. PATENT DOCUMENTS

| 3,828,768 A | 8/1974 | Douglas ............... 128/2.06 A |
| 3,939,824 A | 2/1976 | Arneson et al. ........ 128/2.05 A |
| 3,998,214 A | 12/1976 | Garrison ............... 128/2.06 A |
| 4,000,461 A | 12/1976 | Barber et al. .............. 324/102 |
| 4,023,564 A | 5/1977 | Valiquette et al. ...... 128/206 A |
| 4,336,810 A | 6/1982 | Anderson et al. ........... 128/702 |
| 4,531,527 A | 7/1985 | Reinhold, Jr. et al. ...... 128/696 |
| 4,583,553 A | 4/1986 | Shah et al. ................. 128/704 |
| 4,589,420 A | 5/1986 | Adams et al. |
| 4,637,400 A | 1/1987 | Marcus |

(Continued)

FOREIGN PATENT DOCUMENTS

DE       4405827       6/1995

(Continued)

OTHER PUBLICATIONS

"PCT International Search Report", from International Application No. PCT/US01/45763, dated Sep. 3, 2002,8.

(Continued)

*Primary Examiner*—Ljiljana Ciric
(74) *Attorney, Agent, or Firm*—Schwegman, Lundberg, Woessner & Kluth (57) ABSTRACT

A method for curvature based complex identification and classification comprises sensing a cardiac signal and computing curvatures at sample points on the sensed cardiac signal. Then to extract features from the computed curvatures, and compare the extracted features with a set of predetermined templates, and then to classify the sensed cardiac signal based on the outcome of the comparison.

20 Claims, 4 Drawing Sheets

U.S. PATENT DOCUMENTS

| | | | |
|---|---|---|---|
| 4,721,114 A | 1/1988 | DuFault et al. ............. 128/696 |
| 4,802,491 A | 2/1989 | Cohen et al. ................ 600/509 |
| 4,809,697 A | 3/1989 | Causey, III et al. ... 128/419 PT |
| 4,825,869 A | 5/1989 | Sasmor et al. ......... 128/419 PT |
| 4,832,038 A | 5/1989 | Arai et al. |
| 4,838,278 A | 6/1989 | Wang et al. ................ 128/697 |
| 4,884,345 A | 12/1989 | Long ............................ 33/1 C |
| 4,924,875 A | 5/1990 | Chamoun ................... 128/696 |
| 4,945,917 A | 8/1990 | Akselrod et al. ............ 128/696 |
| 4,947,857 A | 8/1990 | Albert et al. ................. 128/696 |
| 4,989,610 A | 2/1991 | Patton et al. ................ 128/695 |
| 5,000,189 A | 3/1991 | Throne et al. ............... 128/702 |
| 5,014,284 A | 5/1991 | Langer et al. ................. 375/30 |
| 5,014,698 A | 5/1991 | Cohen et al. ................ 128/419 |
| 5,020,540 A | 6/1991 | Chamoun ................... 128/696 |
| 5,046,504 A | 9/1991 | Albert et al. |
| 5,107,850 A | 4/1992 | Olive .......................... 128/705 |
| 5,109,842 A | 5/1992 | Adinolfi ................. 128/419 D |
| 5,139,028 A | 8/1992 | Steinhaus et al. ........... 128/697 |
| 5,156,148 A | 10/1992 | Cohen ................. 128/419 PG |
| 5,184,615 A | 2/1993 | Nappholz et al. ..... 128/419 PG |
| 5,193,550 A | 3/1993 | Duffin ........................ 129/697 |
| 5,201,321 A | 4/1993 | Fulton |
| 5,215,098 A | 6/1993 | Steinhaus et al. ........... 128/702 |
| 5,217,021 A | 6/1993 | Steinhaus et al. ........... 128/702 |
| 5,240,009 A | 8/1993 | Williams .................... 128/702 |
| 5,247,021 A | 9/1993 | Fujisawa et al. ............ 525/254 |
| 5,255,186 A | 10/1993 | Steinhaus et al. ........... 364/413 |
| 5,269,301 A | 12/1993 | Cohen ............................ 607/6 |
| 5,271,411 A | 12/1993 | Ripley et al. ................ 128/702 |
| 5,273,049 A | 12/1993 | Steinhaus et al. ........... 128/696 |
| 5,275,621 A | 1/1994 | Mehra ............................ 607/5 |
| 5,280,792 A | 1/1994 | Leong et al. ................ 128/702 |
| 5,291,400 A | 3/1994 | Gilham |
| 5,292,341 A | 3/1994 | Snell ............................ 607/30 |
| 5,292,348 A | 3/1994 | Saumarez et al. .............. 607/5 |
| 5,311,874 A | 5/1994 | Baumann et al. ........... 128/705 |
| 5,312,445 A | 5/1994 | Nappholz et al. .............. 607/9 |
| 5,313,953 A | 5/1994 | Yomtov et al. ............. 128/696 |
| 5,330,504 A | 7/1994 | Somerville et al. ............ 607/5 |
| 5,331,966 A | 7/1994 | Bennett et al. .............. 128/696 |
| 5,342,402 A | 8/1994 | Olson et al. |
| 5,350,406 A | 9/1994 | Nitzsche et al. .............. 607/14 |
| 5,351,696 A | 10/1994 | Riff et al. |
| 5,360,436 A | 11/1994 | Alt et al. ....................... 607/18 |
| 5,366,487 A | 11/1994 | Adams et al. ................... 607/5 |
| 5,388,578 A | 2/1995 | Yomtov et al. ............. 128/642 |
| 5,400,795 A | 3/1995 | Murphy et al. ............. 128/702 |
| 5,411,031 A | 5/1995 | Yomtov ...................... 128/706 |
| 5,411,529 A | 5/1995 | Hudrlik .......................... 607/6 |
| 5,417,221 A | 5/1995 | Sickler ........................ 128/696 |
| 5,421,830 A | 6/1995 | Epstein et al. ................ 607/30 |
| 5,431,693 A | 7/1995 | Schroeppel |
| 5,447,519 A | 9/1995 | Peterson ........................ 607/5 |
| 5,447,524 A | 9/1995 | Alt ................................ 607/19 |
| 5,456,261 A | 10/1995 | Luczyk ....................... 128/702 |
| 5,458,620 A | 10/1995 | Adams et al. |
| 5,458,623 A | 10/1995 | Lu et al. ....................... 607/28 |
| 5,464,433 A | 11/1995 | White et al. .................... 607/5 |
| 5,478,807 A | 12/1995 | Cronin et al. ................ 514/12 |
| RE35,148 E | 1/1996 | Lizzi et al. .................. 348/163 |
| 5,480,412 A | 1/1996 | Mouchawar et al. |
| 5,503,159 A | 4/1996 | Burton ........................ 128/703 |
| 5,509,927 A | 4/1996 | Epstein et al. ................ 607/32 |
| 5,511,554 A | 4/1996 | Helfenbein et al. |
| 5,513,644 A | 5/1996 | McClure et al. ............ 128/708 |
| 5,520,191 A | 5/1996 | Karlsson et al. ............ 128/702 |
| 5,542,430 A | 8/1996 | Farrugia et al. ............ 128/705 |
| 5,545,186 A | 8/1996 | Olson et al. |
| 5,549,641 A | 8/1996 | Ayers et al. |
| 5,549,654 A | 8/1996 | Powell ......................... 607/32 |
| 5,560,369 A | 10/1996 | McClure et al. ............ 128/704 |
| 5,605,159 A | 2/1997 | Smith et al. |
| 5,609,158 A | 3/1997 | Chan .......................... 128/705 |
| 5,622,178 A | 4/1997 | Gilham ....................... 128/696 |
| 5,628,326 A | 5/1997 | Arand et al. ................ 128/706 |
| 5,634,468 A | 6/1997 | Platt et al. ................... 128/696 |
| 5,645,070 A | 7/1997 | Turcott ....................... 128/702 |
| 5,676,153 A | 10/1997 | Smith et al. |
| 5,682,900 A | 11/1997 | Arand et al. |
| 5,682,902 A | 11/1997 | Herleikson ................. 128/708 |
| 5,683,425 A | 11/1997 | Hauptmann .................... 607/9 |
| 5,685,315 A | 11/1997 | McClure et al. ............ 128/708 |
| 5,687,737 A | 11/1997 | Branham et al. ........... 128/710 |
| 5,704,365 A | 1/1998 | Albrecht et al. ............ 128/702 |
| 5,712,801 A | 1/1998 | Turcott ....................... 364/550 |
| 5,713,366 A | 2/1998 | Armstrong et al. |
| 5,713,367 A | 2/1998 | Arnold et al. .............. 128/704 |
| 5,718,242 A | 2/1998 | McClure et al. ............ 600/515 |
| 5,724,985 A | 3/1998 | Snell et al. ................. 128/697 |
| 5,730,142 A | 3/1998 | Sun et al. ................... 128/705 |
| 5,738,104 A | 4/1998 | Lo et al. ..................... 128/706 |
| 5,738,105 A | 4/1998 | Kroll .......................... 128/708 |
| 5,755,739 A | 5/1998 | Sun et al. ..................... 607/14 |
| 5,759,158 A | 6/1998 | Swanson .................... 600/508 |
| 5,772,604 A | 6/1998 | Langberg et al. ........... 600/518 |
| 5,778,881 A | 7/1998 | Sun et al. ................... 128/696 |
| 5,779,645 A | 7/1998 | Olson et al. ................ 600/518 |
| 5,782,888 A | 7/1998 | Sun et al. ..................... 607/27 |
| 5,792,065 A | 8/1998 | Xue et al. ................... 600/516 |
| 5,792,066 A | 8/1998 | Kwong ....................... 600/517 |
| 5,795,303 A | 8/1998 | Swanson et al. ............ 600/509 |
| 5,797,399 A | 8/1998 | Morris et al. ............... 128/705 |
| 5,797,849 A | 8/1998 | Vesely et al. ............... 600/461 |
| 5,810,739 A | 9/1998 | Bornzin et al. |
| 5,817,133 A | 10/1998 | Houben ......................... 607/9 |
| 5,819,007 A | 10/1998 | Elghazzawi .................. 395/51 |
| 5,819,741 A | 10/1998 | Karlsson |
| 5,827,195 A | 10/1998 | Lander ....................... 600/509 |
| 5,827,197 A | 10/1998 | Bocek et al. ............... 600/518 |
| 5,836,889 A | 11/1998 | Wyborny et al. |
| 5,848,972 A | 12/1998 | Triedman et al. ........... 600/508 |
| 5,855,593 A | 1/1999 | Olson et al. |
| 5,857,977 A | 1/1999 | Caswell et al. ............. 600/518 |
| 5,858,977 A | 1/1999 | Aukerman et al. ........... 514/12 |
| 5,868,680 A | 2/1999 | Steiner et al. ............... 600/518 |
| 5,873,897 A | 2/1999 | Armstrong et al. |
| 5,935,082 A | 8/1999 | Albrecht et al. ............ 600/515 |
| 5,941,831 A | 8/1999 | Turcott |
| 5,944,744 A | 8/1999 | Paul et al. |
| 5,954,661 A | 9/1999 | Greenspon et al. ......... 600/510 |
| 5,957,857 A | 9/1999 | Hartley ....................... 600/521 |
| 5,978,707 A | 11/1999 | Krig et al. |
| 5,984,954 A | 11/1999 | Cohen ........................ 607/521 |
| 5,991,656 A | 11/1999 | Olson et al. |
| 5,991,657 A | 11/1999 | Kim |
| 6,016,442 A | 1/2000 | Hsu et al. |
| 6,024,705 A | 2/2000 | Schlager et al. |
| 6,076,014 A | 6/2000 | Alt |
| 6,091,990 A | 7/2000 | Hsu et al. |
| 6,108,577 A | 8/2000 | Benser ........................ 600/517 |
| 6,161,037 A | 12/2000 | Cohen ........................ 600/513 |
| 6,192,273 B1 | 2/2001 | Igel et al. ..................... 607/14 |
| 6,212,428 B1 | 4/2001 | Hsu et al. .................... 600/515 |
| 6,223,078 B1 | 4/2001 | Marcovecchio ................ 607/5 |
| 6,233,072 B1 | 5/2001 | Liu et al. .................... 359/110 |
| 6,233,078 B1 | 5/2001 | Harano et al. .............. 359/134 |
| 6,233,487 B1 | 5/2001 | Mika et al. ................... 607/27 |
| 6,253,102 B1 | 6/2001 | Hsu et al. |
| 6,263,242 B1 | 7/2001 | Mika et al. ..................... 607/9 |
| 6,266,554 B1 | 7/2001 | Hsu et al. .................... 600/515 |
| 6,272,377 B1 | 8/2001 | Sweeney et al. |
| 6,275,732 B1 | 8/2001 | Hsu et al. ..................... 607/14 |
| 6,301,503 B1 | 10/2001 | Hsu et al. ..................... 607/30 |

| | | | |
|---|---|---|---|
| 6,308,095 B1 | 10/2001 | Hsu et al. ............... 600/518 |
| 6,312,388 B1 | 11/2001 | Marcovecchio et al. .... 600/508 |
| 6,370,430 B1 | 4/2002 | Mika et al. ............... 607/9 |
| 6,430,435 B1 | 8/2002 | Hsu et al. ............... 600/518 |
| 6,434,417 B1 | 8/2002 | Lovett ............... 600/509 |
| 6,449,503 B1 | 9/2002 | Hsu ............... 600/518 |
| 6,484,055 B1 | 11/2002 | Marcovecchio ............... 607/5 |
| 6,516,219 B1 | 2/2003 | Street |
| 6,516,225 B1 | 2/2003 | Florio |
| 6,539,257 B1 | 3/2003 | KenKnight |
| 6,684,100 B1 | 1/2004 | Sweeney et al. ............ 600/517 |
| 6,708,058 B2 | 3/2004 | Kim et al. |
| 6,728,572 B2 | 4/2004 | Hsu et al. |
| 6,745,068 B2 | 6/2004 | Koyrakh et al. |
| 6,760,615 B2 | 7/2004 | Ferek-Petric |
| 6,766,190 B2 | 7/2004 | Ferek-Petric |
| 6,889,081 B2 | 5/2005 | Hsu |
| 6,950,702 B2 | 9/2005 | Sweeney |
| 2002/0032469 A1 | 3/2002 | Marcovecchio |
| 2002/0087091 A1 | 7/2002 | Koyrakh et al. |
| 2002/0091333 A1 | 7/2002 | Hsu et al. |
| 2002/0183637 A1 | 12/2002 | Kim et al. |
| 2002/0183639 A1 | 12/2002 | Sweeney et al. |
| 2003/0083586 A1 | 5/2003 | Ferek-Petric |
| 2003/0083587 A1 | 5/2003 | Ferek-Petric |
| 2003/0100923 A1 | 5/2003 | Bjorling et al. |
| 2003/0181818 A1 | 9/2003 | Kim et al. |
| 2004/0010200 A1 | 1/2004 | Sweeney |
| 2004/0093035 A1 | 5/2004 | Schwartz et al. |
| 2004/0127806 A1 | 7/2004 | Sweeney |
| 2004/0176694 A1 | 9/2004 | Kim et al. |
| 2005/0159781 A1 | 7/2005 | Hsu et al. |

FOREIGN PATENT DOCUMENTS

| | | |
|---|---|---|
| EP | 469817 A2 | 7/1991 |
| EP | 0 469 817 A2 | 2/1992 |
| EP | 0469817 | 2/1992 |
| EP | 506230 A1 | 2/1992 |
| EP | 0 506 230 | 9/1992 |
| EP | 0506230 | 9/1992 |
| EP | 0554208 | 8/1993 |
| EP | 0711531 | 5/1996 |
| EP | 0776630 | 11/1996 |
| EP | 0776631 | 11/1996 |
| EP | 0848965 | 6/1998 |
| WO | WO97/39681 | 10/1997 |
| WO | WO-98/53879 | 12/1998 |
| WO | WO-99/65570 | 12/1999 |
| WO | WO-9965570 A1 | 12/1999 |
| WO | WO-00/10455 | 3/2000 |
| WO | WO-00/47278 | 8/2000 |
| WO | WO-0047278 A1 | 8/2000 |

OTHER PUBLICATIONS

Duru, Firat, et al., "The Potential for Inappropriate Ventricular Tachycardia Confirmation Using the Intracardiac Electrogram (EGM) Width Criterion", *PACE*, vol. 22, (Jul. 1999),1039-1046.

Grady, Thomas A., et al., "Prognostice Significance of Exercise-Induced Left Bundle-Branch Block", *JAMA*, vol. 279, No. 2, Jan. 14, 1998,153-156.

IEEE, "Microcomputer-Based Telemetry System for ECG Monitoring", *IEEE Proc. of the Ann. Int'l Conf. of the Engineering in Medicine and Biology Society*, vol. Conf. 9, XP000015425, (1987),1492-193.

Kinoshita, Shinji, et al., "Transient Disappearance of Complete Right Bundle Branch (BBB) During Exercise", *Journal of Electrocardiology*, vol. 29, No. 3, 1996,255-256.

Sweeney, Robert J., "Signal Compression Based on Curvature Parameters", U.S. Appl. No. 10/607,820, filed Jun. 27, 2003, 50 pgs.

Sweeney, Robert J., et al., "Tachyarrahythmia Detection and Discrimination Based on Curvature Parameters", U.S. Appl. No. 10/607,818, filed Jun. 27, 2003, 59 pgs.

Vapnik, V. N., "Chapter 5 Constructing Learning Algorithms", *The Nature of Statistical Learning Theory*, Springer-Verlag New York, Inc.,(1995),119-166.

Afonso, V. X., et al., "ECG Beat Detection Using Filter Banks", *IEEE Transactions on Biomedical Engineering*, 46, (Feb. 1999),192-202.

Afonso, V. X., et al., "Filter Bank-based ECG Beat Classification", *Proceedings of the 19th International Conference—IEEE/EMBS*, Chicago, IL,(Oct. 30-Nov. 2, 1997),97-100.

Afonso, V. X., et al., "Filter Bank-based ECG Beat Detection", *Proceedings of the 18th Annual International Conference of the IEEE Engineering in Medicine and Biology Society*, Amsterdam, The Netherlands,(1996),1037-1038.

Afonso, V. X., et al., "Filter Bank-based Processing of the Stress ECG", *1995 IEEE-EMBC and CMBEC—Theme 4: Signal Processing*, (1995),887-888.

Afonso, V. X., et al., "Multirate Processing of the ECG using Filter Banks", *Computers in Cardiology*, (1996),245-248.

CURVATURE BASED METHOD FOR SELECTING FEATURES FROM AN ELECTROPHYSIOLOGIC SIGNAL FOR PURPOSE OF COMPLEX IDENTIFICATION AND CLASSIFICATION

CROSS-REFERENCE TO RELATED APPLICATION(S)

This application is a continuation of U.S. patent application Ser. No. 09/703,269, filed on Oct. 31, 2000, now issued as U.S. Pat. No. 6,684,100, the specification of which is incorporated herein by reference.

FIELD OF THE INVENTION

The present invention relates generally to cardiac rhythm management systems, and more particularly, it pertains to a system and method of classification and detection of cardiac signals.

BACKGROUND OF THE INVENTION

Analysis of cardiac signals, which is routinely performed in electrocardiography is generally based on visual inspection to quantify or qualify wave morphology for the purpose of identifying and classifying abnormal patterns. Certain morphological characteristics of commonly recorded signals have high diagnostic value. The shape and inter arrival times of R-waves recorded in the electrocardiogram generally provide a wealth of information about the state of the heart. Accordingly, automated approaches for identifying and classifying abnormalities in signals such as cardiac signals have sought to use a signal's significant morphologic characteristics.

However, given the wide diversity of possible shapes for cardiac signals, it is usually not possible for an automatic approach to identify significant characteristics that can be used for unambiguous classification. Rather, automated classification approaches generally compare the entire morphological shape of a signal with the shape of similar signals with known abnormalities but without particular regard to the specific characteristics that the signals contain. Alternatively, automated classification approaches restrict the automated examination only to those signals which are essentially normal and use detailed metrics (for example QRS width, QT interval or ST segment amplitude) of the essentially normal morphology for classifying abnormalities.

Despite its importance in the analysis of biologic signals, the automated and accurate identification and quantification of the significant morphological characteristics (for example turns, peaks, knees, inflection points, and the like) in any cardiac signal (both abnormal as well as normal) is still in a developing stage. Existing methods have used the concept of sharpness (for example to detect R-waves) but have had limited success. This is due in part to the overly simplistic mathematical treatment this concept has received, as reflected in the rudimentary algorithms used for these measurements. Most of the current detection methods rely on three point interpolations to measure sharpness. The simplest and most commonly used methods for measuring peaks of R-waves are based upon Taylor-series approximations to estimate the second derivative of the sensed signal. This formula utilizes highly local information (the point at the peak and its two close neighbors) ignoring nearby points which may contribute to signal peak. Other popular approaches utilize less local data, such as the peak and two adjacent extrema. All of these methods, which rely on three-point estimates of sharpness, may produce inaccurate estimates, if waveforms are complex or are contaminated with noise. Thus, a need exists for automated identification and classification of peaks, knees, inflection points, and the like in sensed cardiac signals that takes into account wave scale and complexity that can yield a more accurate estimate of peaks for identifying and classifying abnormalities in cardiac signals.

SUMMARY OF THE INVENTION

The present subject matter provides a curvature based method of selecting features from electrophysiologic signals for purpose of complex identification and classification. According to one aspect of the present subject matter, this is accomplished by sensing a cardiac signal (sensing the cardiac signal includes sensing complexes continuously on a real-time basis) and computing curvatures on a sample point-by-sample point basis $(X_1, X_2, X_3, \ldots X_I)$ on the sensed cardiac signal on a continuous basis. In one embodiment, the curvature at the sample points $X_1, X_2, X_3, \ldots X_I$ are computed by fitting a cubic least square error curve (using N number of sample points) to the sensed cardiac signal. In this embodiment, N is an odd number, and the sample point (where the curvature is computed) is at a mid point of the N number of sample points.

Also on a continuous basis, features of significant interest are extracted from the computed curvatures. In some embodiments, this is accomplished by comparing the computed curvatures at the sample points $X_1, X_2, X_3, \ldots X_I$ to a set of predetermined threshold values. In some embodiments, the features are extracted based on computing features such as a time when the feature occurs, an amplitude of the feature, and other similar features at each of the sample points and comparing them to a set of threshold values.

Also on a continuous basis a set of features associated with a first complex in the sensed cardiac signal are identified and separated from the continuously computed and extracted features upon detecting a second subsequent complex. The second subsequent complex is a complex that is adjacent to the first complex and occurs substantially immediately after the first complex. This process of identifying and separating extracted features repeats itself from one sensed complex to another subsequent sensed complex on a real time basis. One reason for identifying and separating the set of features associated with the first complex is to prevent the features associated with the first complex from mixing with the features associated the second subsequent complex. Separating the features associated with first complex aids in classifying the sensed first complex.

Next, the process includes identifying a fiducial feature from the separated set of extracted features associated with the first complex and aligning the separated set of features with respect to the identified fiducial feature. In one embodiment, fiducial feature is identified based on comparing the times when each of the separated set of features occur with a time when a complex associated with the separated set of features is detected on the sensed cardiac signal, and selecting a feature from the separated set of features that is closest in time to the time when the complex associated with the separated set of features was detected. One reason for using a time when a complex is detected (such as R wave) in identifying the fiducial feature, is because the detection of a complex in a sensed cardiac signal is generally more reliable and consistent.

Next, the process includes aligning the separated set of features around the identified fiducial feature. Aligning the separated set of features around the identified fiducial feature aids in normalizing each of the separated set of feature around a datum such as the associated detected complex, and further aids in comparing the separated set of features with a set of predetermined templates.

Next the process includes comparing the aligned set of features to a set of predetermined templates to classify the associated complex. In some embodiments, the predetermined templates are a set of identified complexes associated with known cardiac arrhythmias that would assist in comparing and classifying the extracted set of features. In some embodiments, a therapy is provided to the heart based on the outcome of the classification. The above described process repeats itself on a continuous basis for a real-time classification of complexes from the sensed cardiac signal.

Other aspects of the invention will be apparent on reading the following detailed description of the invention and viewing the drawings that form a part thereof.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

Analysis of cardiac signals, which is routinely performed in electrocardiography is generally based on visual inspection to quantify or qualify wave morphology for the purpose of identifying and classifying abnormal patterns. Certain morphological characteristics of commonly recorded signals have high diagnostic value. The shape and inter arrival times of R-waves recorded in the electrocardiogram generally provide a wealth of information about the state of the heart. Accordingly, automated approaches for identifying and classifying abnormalities in signals such as cardiac signals have sought to use a signal's significant morphologic characteristics.

However, given the wide diversity of possible shapes for cardiac signals, it is usually not possible for an automatic approach to identify significant characteristics that can be used for unambiguous classification. Rather, automated classification approaches generally compare the entire morphological shape of a signal with the shape of similar signals with known abnormalities but without particular regard to the specific characteristics that the signals contain. Alternatively, automated classification approaches restrict the automated examination only to those signals which are essentially normal and use detailed metrics (for example QRS width, QT interval or ST segment amplitude) of the essentially normal morphology for classifying abnormalities.

Despite its importance in the analysis of biologic signals, the automated and accurate identification and quantification of the significant morphological characteristics (for example turns, peaks, knees, inflection points, and the like) in any cardiac signal (both abnormal as well as normal) is still in a developing stage. Existing methods have used the concept of sharpness (for example to detect R-waves) but have had limited success. This is due in part to the overly simplistic mathematical treatment this concept has received, as reflected in the rudimentary algorithms used for these measurements. Most of the current detection methods rely on three point interpolations to measure sharpness, may produce inaccurate estimates, if waveforms are complex or are contaminated with noise.

GENERAL SYSTEM OVERVIEW

The present subject matter provides, among other things, a system of classifying a cardiac signal by computing a curvature versus time signal from a sensed cardiac signal and comparing the computed curvature versus time signal with a set of predetermined templates. The present system also provides an automated identification and classification of peaks, knees, inflection points, and the like in cardiac signals that takes into account wave scale and complexity that can yield a more accurate classification of cardiac signals.

The first step in the process includes computing continuously a curvature versus time signal from a sensed cardiac signal on a real-time basis. The process also includes extracting features (features are generally significant points of interest on the sensed cardiac signal) continuously on a real-time basis from the computed curvature versus time signal. Next, the process includes continuously separating a set of features associated with a first complex upon detecting a second subsequent complex so that each individual complex can be identified and classified on a real-time basis. Then the process includes aligning and classifying the extracted and separated set of features by comparing the separated set of features with a set of predetermined templates. Other aspects of the invention will be apparent on reading the following detailed description of the invention and viewing the drawings that form a part thereof.

Figure 1:
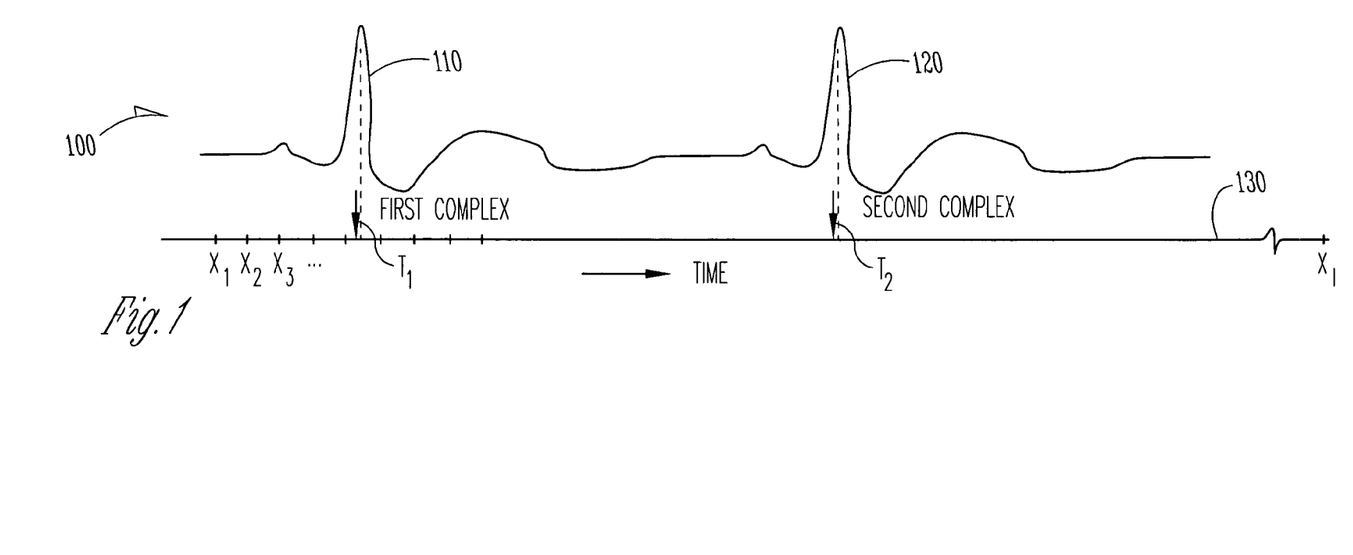
FIG. 1 is a cardiac signal according to one aspect of the present invention.

Referring now to FIG. 1, there is one embodiment of the first step in the process of sensing a cardiac signal 100 according to the present invention. Shown in FIG. 1 are detection of heart beats associated with first and second complexes 110 and 120 at times '$t_1$' and '$t_2$' associated with the sensed cardiac signal 100 on a real-time basis on a time line 130. Also, shown on the time line 130 are the various sample points $X_1$, $X_2$, $X_3$, . . . $X_I$ used in computing a curvature versus time signal on the first complex 110. In the example embodiment shown in FIG. 1, the sample points can be some fixed interval of time, such as 2, 4, 6 . . . milliseconds, at which curvatures are computed on the sensed cardiac signal. Also shown in this embodiment, is the detection of the complexes (110, 120, and so on) on a continuous basis on the sensed cardiac signal 100.

Figure 2:
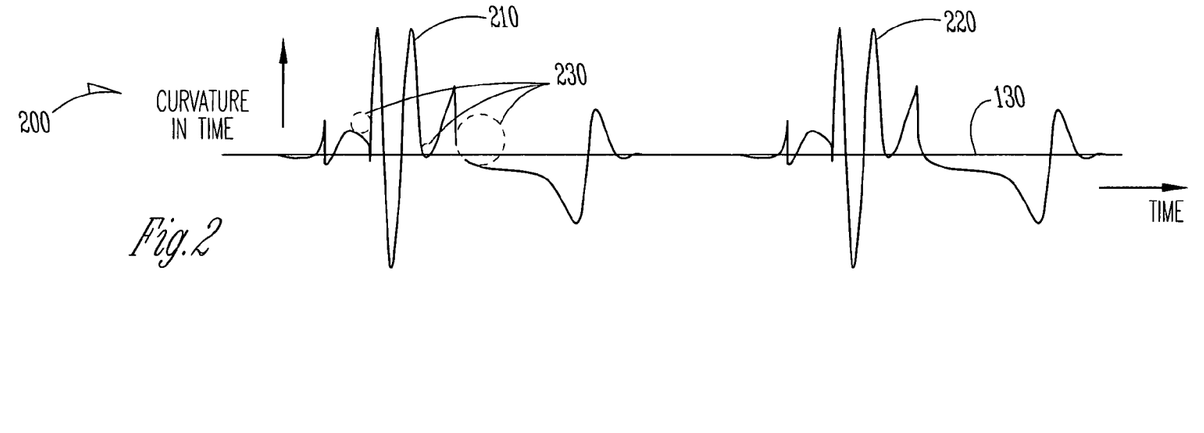
FIG. 2 is a curvature figure derived from the cardiac signal of FIG. 1 according to one aspect of the present invention.

Referring now to FIG. 2, there is shown one embodiment of generating a curvature versus time signal 200 on a real-time basis derived from the sensed cardiac signal 100 shown in FIG. 1 according to the present invention. FIG. 2 is also on the same time line 130 as in FIG. 1. Curvature FIG. 200 shown in FIG. 2 is a computed curvature (expressed in time) versus time signal generated continuously by computing curvatures at the sample points $X_1$, $X_2$, $X_3$, ... $X_I$ on the sensed cardiac signal 100 shown in FIG. 1. Curvature FIGS. 210 and 220 are computed curvature versus time signals associated with first and second complexes 110 and 120 shown in FIG. 1, respectively. In this example embodiment, the curvature versus time signal is computed by overcoming the dimensionality of the curvature by changing the dimensionality of the curvature to time. The reason for overcoming the dimensionality of the curvature is to convert the time versus voltage signal, which is time versus curvature, to a time versus time signal to facilitate easier computation of curvature (for example, when a curve exists in length-length space, the quantity has dimension of length and is traditionally called the radius of curvature, and if the curve exists in time-time space, the analogous quantity will be called the radius of time). In this time-time space the curvature has a dimension of 1/Time. Also, shown in FIG. 2 are some example sample points 230 at which curvatures are computed.

Figure 3A:
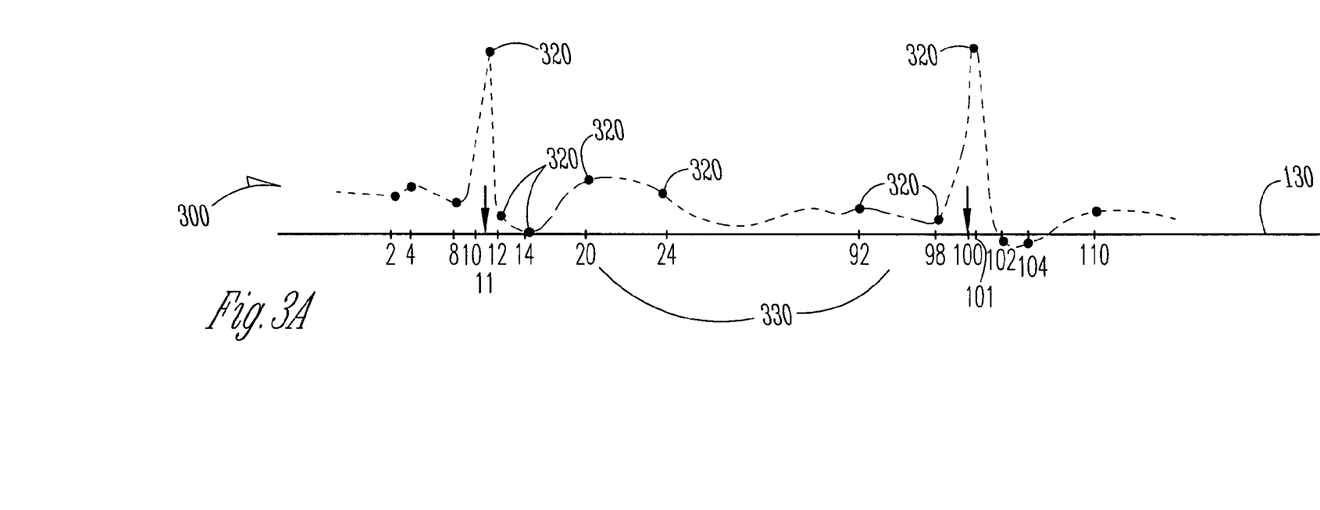
FIGS. 3A and 3B illustrate separating and aligning features derived from the curvature figure of FIG. 2 according to one aspect of the present invention.

Referring now to FIGS. 3A and 3B, there is shown one example embodiment of extracting and aligning 300 sets of features associated with respective detected complexes. FIG. 3A, illustrates continuously extracting features 320 from the computed curvature versus time signal 200 shown in FIG. 2. Also shown in this example embodiment, are some sample times in milliseconds 330 when the extracted features occur on the time line 130. FIG. 3A is also on the same time as that of FIGS. 1 and 2. In the example embodiment shown in FIG. 3A, the sample times (where the curvatures are computed) have a fixed interval of 2 milliseconds. Also, in this example embodiment, the beat associated with first complex 110 is detected at 11 milliseconds ($t_1$) and the beat associated with the second subsequent complex 120 is detected at 101 milliseconds ($t_2$).

Figure 3B:
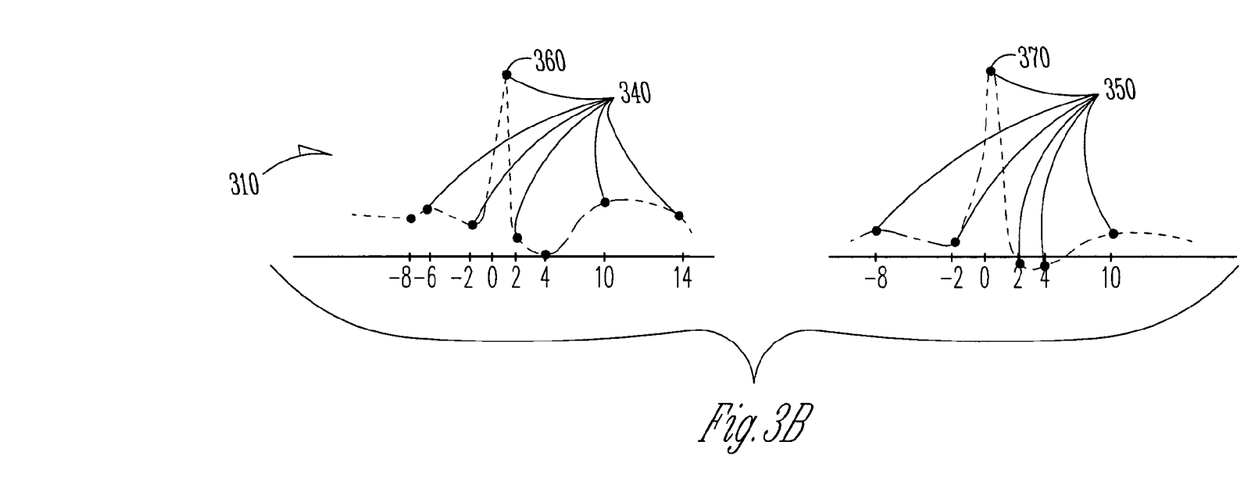

FIG. 3B shows separating sets of extracted features 310 associated with the complexes 110, 120 ... on a continuous basis from the continuously extracted features 320 shown in FIG. 3A. In the example embodiment shown in FIG. 3B, a set of features 340 associated with first complex is separated upon detecting the second subsequent complex 120. Also shown are separating a set of features 350 associated with second complex upon detecting a third subsequent complex. This process of separating a set of features associated with a complex is done on a continuous basis. Features associated with first complex is separated from the features of subsequent second complex in order to (so that the features are not mingled with the extracted features of the second subsequent complex) classify the sensed first complex 110. The next step is to identify fiducial features 360, 370, and so on. In the example embodiment shown in FIG. 3B, fiducial feature 360 is identified based on comparing times when the separated sets of extracted features associated with the first complex 110 occur with a time when the heart beat associated with the first complex 110 is detected ('$t_1$'), and choosing a feature from the set of features 340 that is closest in time to the time when the heart beat associated with the first complex 110 is detected. In the example shown in FIG. 1, the first complex 110 is detected at 11 milliseconds. The times when the separated set of features 340 associated with the first complex 110 occur are 2, 4, 8, 10, 12, 14, 20, and 24 milliseconds as shown in FIG. 3A. Based on comparing the times when the separated set of features 340 occur with the time when first complex 110 was detected, the feature 360 that occurs at a time of 10 milliseconds is the closest in time to the detected first complex 110 which occurs at 11 milliseconds. Therefore, extracted feature 360 is selected as the fiducial feature from the separated set of features 340 associated with the first complex 110. Similarly, the extracted feature 370 is selected as the fiducial feature for the separated set of features 350 associated with subsequent second complex 120. This process repeats itself continuously on a real time basis. In some embodiments, the fiducial feature is identified from the set of separated features associated with the first complex based on a predetermined deviation value. The predetermined deviation value is based on a sample point having an amplitude farthest from a predetermined reference point.

The next step is to align the separated set of features 340 associated with the first complex 110, and to classify the separated set of features 340 by comparing the aligned set of features with a set of templates. Separated sets of features 340 and 350 are aligned to normalize the separated sets of feature 340 and 350 so that the aligned features aid in comparing the separated sets of features with a template to classify the sensed complexes 110 and 120. FIG. 3B, illustrates one example embodiment of aligning the set of extracted features 340 (associated with first complex 110) with respect to an identified fiducial feature 360. In this example embodiment, the time when the identified fiducial feature occurs (at 10 milliseconds) is subtracted from each of the times when the separated set of features 340 associated with the first complex 110 occurs (at 2, 4, 8, 10, ... milliseconds) to arrive at aligned times −8, −6, −2, 0, 2, 4, 10, and 14 milliseconds for the separated set of features 340. Similarly, the aligned times −8, −2, 0, 2, 4, and 10 are computed for the separated set of features 350 associated with the second complex 120. This process of aligning separated set of features continues on a real time basis for the detected complexes on the sensed cardiac signal 100. It can be seen from the above illustrated computation, that the process aligning helps normalize the times associated with each of the separated sets of features, and how it aids in comparing the separated set of features 340 and 350 with a set of templates and in classifying the sensed complexes 110 and 120.

Figure 4:
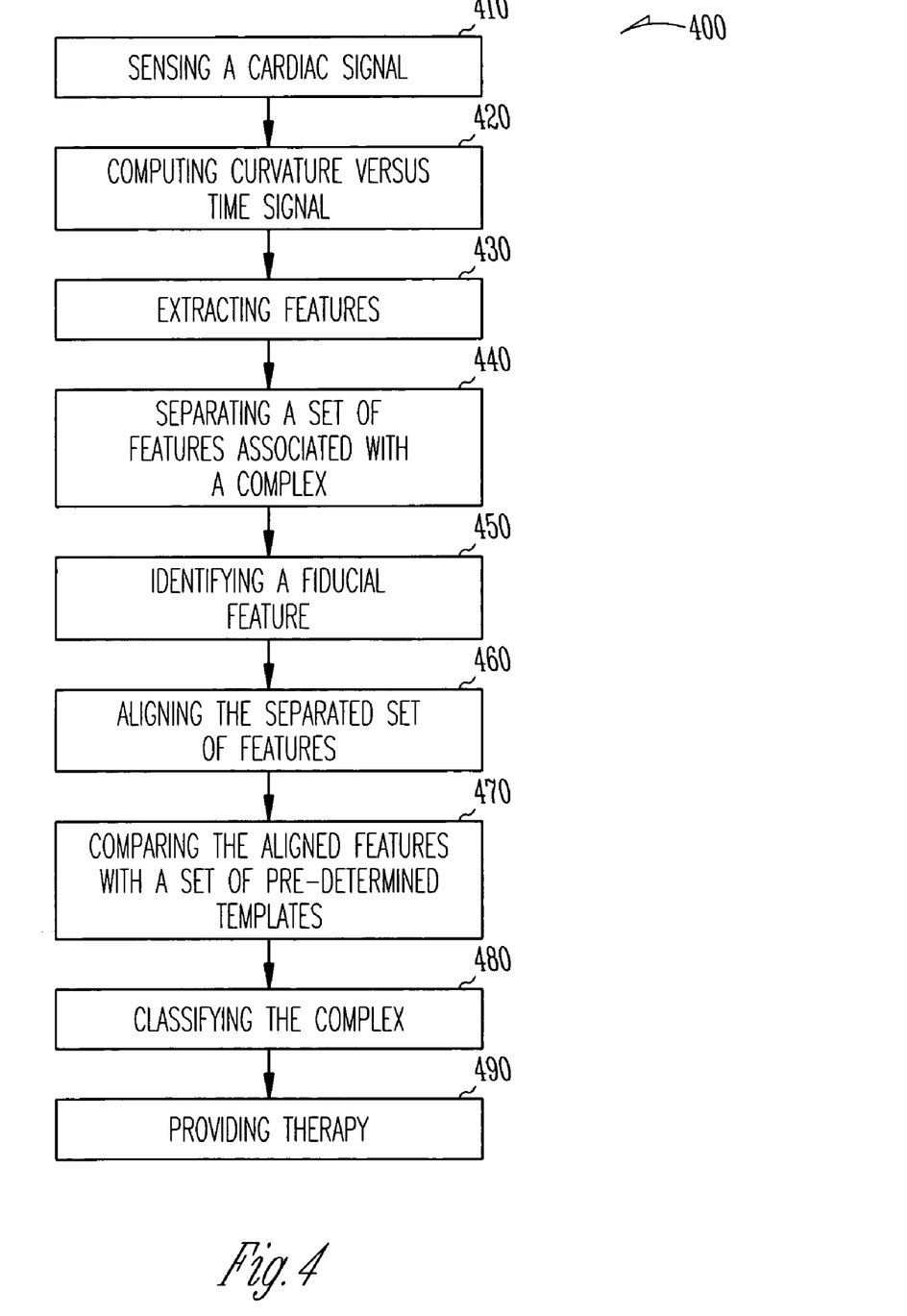
FIG. 4 is a flow diagram illustrating generally one embodiment of operation of the present subject matter.

FIG. 4, illustrates a method 400 of identifying and classifying a sensed cardiac signal on a real-time basis. Method 400, as shown in FIG. 4, begins with step 410 by sensing a cardiac signal 410 from the one or more electrodes disposed in or around a heart 515 on a continuous basis.

The next step 420 in the process comprises computing curvatures at sample points $X_1, X_2, X_3, \ldots X_I$ on the sensed cardiac signal. In some embodiments, the sample points $X_1$, $X_2, X_3, \ldots X_I$ are fixed intervals of time at which the sensed cardiac signal is computed for its curvature. The sensed cardiac signal can be an atrial or ventricular signal of a heart. In one embodiment, the curvatures at sample point $X_1$, $X_2$, $X_3, \ldots X_I$ is computed by fitting a cubic least square error curve to the sensed cardiac signal by using N sample points. In this embodiment, N is an odd number greater than or equal to 5. Also in this embodiment, the cardiac rhythm management system computes the curvature at a mid point of the N sample points. In one embodiment, the cardiac rhythm management system computes curvature (K) at a sample point $X_I$ on the cardiac signal by using 5 sample points over which the cubic fit is (N being 5 in this example) made using $$K=(2C_I/(1+B_I^2)^{3/2})$$

where $$B_I=T_1Y(I-2)+T_2Y(I-1)+T_3Y(I)+T_4Y(I+1)+T_5Y(I+2)$$

$$C_I=S_1Y(I-2)+S_2Y(I-2)+S_3Y(I)+S_4Y(I+1)+S_5Y(I+2)$$

where $S_1$, $S_2$, $S_3$ ... and $T_1$, $T_2$, $T_3$ ... are constant terms in the summation. In this embodiment, I corresponds to the sample point at which the curvature is being computed. For example, if the sample point is $X_3$, then I will be equal to 3 and so on.

In another embodiment, the system computes average curvature between two adjacent sample points by using a linear interpolation of the $B_I$ and $C_I$ between the two adjacent sample points (this is done by doing the integral of the curvature between the two adjacent sample points). This integration helps capture any curvatures that become larger between the two adjacent sample points, so that the pointwise curvature values may more robustly represent the curvatures in the sensed cardiac signal. The system also integrates curvature versus time curve to find the area under the curve. This area under the curve represent the total change in angle between two points on the original cardiac signal. Thus, peaks, turns, inflections, and the like in the cardiac signals can be identified when the curvature versus time curve has peaks or nadirs. These peaks and nadirs denote points along the sensed cardiac signal where the turns are locally sharpest. Also, slow but steady turns on the sensed cardiac signal can be characterized by a small peak having a substantial area under the curvature curve. Thus, integrating curvatures between two adjacent sample points can help capture any curvatures that may become larger between any two adjacent sample points.

In one embodiment, the cardiac rhythm management system computes curvatures at sample points $X_1$, $X_2$, $X_3$, ... $X_I$ on the sensed cardiac signal on a continuous basis.

Then the next step 430 in the process includes extracting features from the computed curvatures by comparing the computed curvatures with a set of predetermined threshold values. FIG. 3A, illustrates extracting features from the computed curvatures at the sample points $X_1$, $X_2$, $X_3$, ... $X_I$. In some embodiments, the set of predetermined threshold values are based on a previous curvature value, a first curvature value, and a curvature threshold limit. In one embodiment, the step of extracting features from the curvature versus time signal is done on a continuous basis on the sensed cardiac signal as shown in FIG. 3A. In some embodiments, the features are defined by one or more metrics. In this embodiment, the one or more metrics are defined as area under a computed curvature, a time of centroid of the area, and a value of original signal amplitude at a time of centroid of the area associated with the feature.

Then the next step 440 comprises separating a set of features associated with a first complex upon detecting a second subsequent complex from the sensed cardiac signal. Separating of extracted features associated with the detected complex is illustrated in detail FIGS. 1, 2, 3A and 3B. In some embodiments, the second subsequent complex is detected based on continuously processing the sensed cardiac signal to produce a signal that is the absolute value of the first derivative of a sensed cardiac signal versus time. Then comparing the produced absolute value versus time signal with a predetermined decaying threshold value to detect an occurrence of the second subsequent complex. In some other embodiments, the second subsequent complex is detected when the absolute value of the first derivative exceeds a predetermined decaying threshold value. In some embodiments, the features associated with the first complex are stored in a memory until the second subsequent complex is detected, and at that point, the features associated with the first complex are replaced by the features associated with the second subsequent complex in the memory. The step of separating can comprise separating the set of features based on selecting features associated with the first complex having a predetermined time earlier than the detected second subsequent complex. In some embodiments, each of the set of features are further compared to an area threshold value to eliminate features less than the area threshold value. This can result in a set of revised features that can represent the first complex.

Then the next step 450 in the process is to identify a fiducial feature from the set of separated features associated with the first complex based on a predetermined deviation value. In some embodiments, fiducial feature is identified based on comparing the time when the first complex occurs with the times when the separated set of features associated with the first complex occur. The process of identifying a fiducial feature is discussed in more detail with respect to FIGS. 3A and 3B.

Then the next step 460 in the process comprises aligning the set of separated features with respect to the identified fiducial feature. The process of aligning is also discussed in more detail in FIG. 3B. The process of aligning helps normalize the times associated with each of the separated set of features and further facilitates in comparing the separated set of features with a set of predetermined templates to classify the detected complex.

Then the next step 470 comprises comparing the aligned set of separated features with a set of predetermined templates. In one embodiment, the set of predetermined templates are one or more known types of heart beat signals. In another embodiment, the set of predetermined templates consists of sets of template boxes or zones for each of the known types of heart beat signals. Generally, each template box or zone can have center amplitude, a time width, and an amplitude width. Also generally, the template boxes or zones for each known type of heart beat can consist of one or more template boxes or zones each of which can have different centers and widths. In this embodiment, the comparing step comprises assigning a score based on how well each feature matches with each of the set of template boxes or zones. In this embodiment, if the separated set of features associated with the first complex fails to match with the set of templates then the complex is assigned with an unknown heart beat classification. In one embodiment, the set of template boxes or zones are modified over time to reflect any changes in sets of separated features used in matching with the template boxes or zones. This can permit known beat type templates to follow slow trends or long-term changes in the cardiac signal.

The next step 480 in the process comprises classifying the detected first complex based on the outcome of the comparison. Then the next step 490 comprises providing a therapy based on the outcome of the classification. In one embodiment, the next step includes guiding a therapy to a heart based on the outcome of the classification. In another embodiment, the next step in the process includes storing classifications for future diagnostic purposes.

Figure 5:
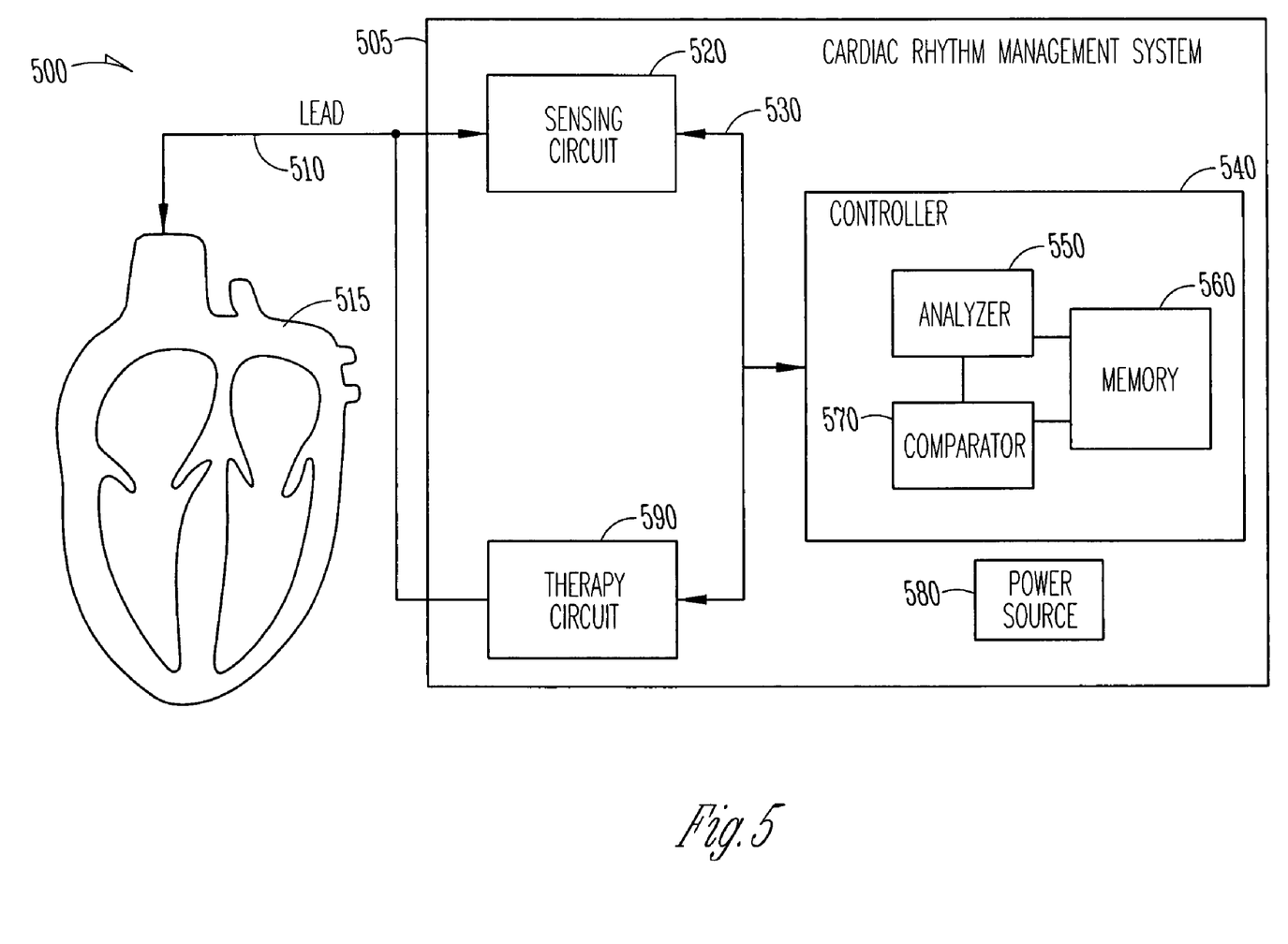
FIG. 5 is a schematic/block diagram illustrating generally one embodiment of portions of a cardiac rhythm management system of the present subject matter.

FIG. 5, is a schematic/block diagram 500 illustrating one embodiment of portions of a cardiac rhythm management system 505, which is coupled to a heart 515. Cardiac rhythm management system 505 includes a power source 580, a controller 540, a sensing circuit 520, a therapy circuit 590, and a via node/bus 530. The sensing circuit 520 is coupled by a lead 510 to the heart 515 for receiving, sensing, and or detecting electrical heart signals. The sensing circuit 520 provides one or more sensed cardiac signals to the controller 540, via the node/bus 530. The controller 540 also controls the delivery of a therapy provided by the therapy circuit 590 and/or other circuits, as discussed below.

The controller 540 includes various modules, which are implemented either in hardware or as one or more sequences of steps carried out on a microprocessor or other controller. Such modules are illustrated separately for conceptual clarity; it is understood that the various modules of the controller 540 need not be separately embodied, but may be combined and/or otherwise implemented, such as in software/firmware.

In general terms, the sensing circuit 520 senses a cardiac signal on a continuous basis from a heart tissue in contact with a catheter lead 510 to which the sensing circuit 520 is coupled. In one embodiment, the sensed cardiac signal is an atrial signal. In another embodiment, the sensed cardiac signal is a ventricular signal. Sensed cardiac signal from the sensing circuit 520 is then received and processed by an analyzer 550 of the controller 540 to compute curvatures continuously on a real-time basis at sample point $X_1$, $X_2$, $X_3$, ... $X_I$ on the sensed cardiac signal. In some embodiments, the sample points are spaced at fixed intervals of time preset by the analyzer 550 on the sensed cardiac signal. In one embodiment, the analyzer 550 computes curvature at sample points $X_1$, $X_2$, $X_3$, ... $X_I$ by fitting a cubic least square error curve to the sensed cardiac signal using N sample points to fit the cubic least square error curve. In one embodiment, the analyzer 550 computes the computing curvature (K) at a sample point $X_I$ on the cardiac signal when using 5 sample points over which the cubic fit is (N being 5 in this example) made using $$K = (2C_I/(1+B_I^2)^{3/2})$$

where $$B_I = T_1 Y(I-2) + T_2 Y(I-1) + T_3 Y(I) + T_4 Y(I+1) + T_5 Y(I+2)$$

$$C_I = S_1 Y(I-2) + S_2 Y(I-2) + S_3 Y(I) + S_4 Y(I+1) + S_5 Y(I+2)$$

where $S_1$, $S_2$, $S_3$ ... and $T_1$, $T_2$, $T_3$ ... are constant terms in the summation. In this example embodiment, I is equal to the point at which the curvature is being computed. For example, if the curvature is being computed at sample point $X_3$, then I will be equal to 3 and so on. In one embodiment, N is an odd number greater than or equal to 5. In this embodiment, the analyzer 550 computes curvature at a midpoint of the N number of sample points.

In another embodiment, the analyzer 550 computes curvature based on an average curvature between two adjacent sample points based on a linear interpolation of the $B_I$ and $C_I$ between two adjacent points (integrating the computed curvatures between the two adjacent sample points). In one embodiment, the analyzer 550 computes the curvatures continuously on a real-time basis from the sensed cardiac signal. Then the analyzer 550 extracts features by comparing the computed curvatures to a set of predetermined threshold values. In one embodiment, the predetermined threshold values are based on a previous curvature value, a curvature value, and a curvature threshold limit. In one embodiment, the analyzer 550 extracts features on a continuous basis. Then the analyzer 550 separates a set of features associated with a first complex upon detecting a second subsequent complex from the sensed cardiac signal. Then the analyzer 550 identifies a fiducial feature from the set of separated features associated with the first complex based on a predetermined deviation value. Then the analyzer 550 further aligns the set of separated features with respect to the identified fiducial feature. In one embodiment, the analyzer 550 separates the set of features associated with the first complex based on a predetermined time earlier than the detected second subsequent complex. In one embodiment, the predetermined deviation value is based on a sample point having an amplitude farthest from a predetermined reference point.

Then a comparator 570 coupled to the analyzer 550, compares the aligned set of features associated with the first complex with a predetermined set of templates, and classifies the first complex based on the outcome of the comparison. In one embodiment, the comparator 570 issues a command signal based on the outcome of the classification. In another embodiment, the therapy circuit 590 coupled to the comparator 570 delivers the electrical energy through the lead 510 to at least one electrode disposed in or around the heart 515 upon receiving the command signal from the comparator 570. The electrical energy delivered by the therapy circuit 590 can be a pacing pulse electrical energy. In one embodiment, the analyzer 550 includes a variable gain circuitry that can adapt according to the changes in the sensed cardiac signal. In one embodiment, the controller 540 includes a memory 560 coupled to the comparator 570 and the analyzer 550 to store the extracted features of the first complex. In another embodiment, the memory 560 stores the classified first complexes for diagnostic purposes.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

CONCLUSION

The above described method provides, among other things, a curvature based complex identification and classification. The process comprises sensing a cardiac signal and computing curvatures at sample points on the sensed cardiac signal, and then to extract features from the computed curvatures. Then to compare the extracted features with a set of predetermined templates, and then to classify the cardiac signal based on the outcome of the comparison.

What is claimed is:

1. A cardiac rhythm management system, comprising:
   at least one electrode;
   a signal sensing circuit coupled to the electrode to sense a cardiac signal, the cardiac signal having signal complexes;
   a controller coupled to the sensing circuit, wherein the controller receives the sensed cardiac signal, and wherein the controller includes:
      memory configured to store signal complexes and to store sets of predetermined templates, the predetermined templates including sets of template zones; and an analyzing module configured to:
compute curvatures at sample points on the sensed cardiac signal,
extract features from the computed curvatures, and
classify the signal complexes by comparing the extracted features to the template zones of the predetermined templates.

2. The system of claim 1, wherein the template zones include a center amplitude, a time width and an amplitude width.

3. The system of claim 2, wherein the template zones include different centers and widths for different types of cardiac signals.

4. The system of claim 3, wherein the controller further includes a scoring module, wherein the scoring module assigns a score to an extracted feature based on how well the feature matches a set of template zones.

5. The system of claim 4, wherein the template zones are modified over time to improve matching with the extracted features.

6. The system of claim 1, wherein the analyzing module is configured to assign an unknown classification to a signal complex when the extracted features fail to match the sets of templates.

7. A method comprising:
sensing a voltage versus time cardiac signal using an implantable medical device;
converting the voltage versus time cardiac signal into a time versus time signal;
computing curvature at sample points on the time versus time signal;
extracting features from the computed curvature;
comparing the extracted features with a set of predetermined templates; and
classifying the cardiac signal based on an outcome of the comparison.

8. The method of claim 7, wherein extracting features from the computed curvatures includes separating a set of features associated with a first cardiac signal complex upon detecting a subsequent second cardiac signal complex.

9. The method of claim 8, wherein separating the set of features includes identifying a fiducial feature from the set of separated features based on comparing the time when the first signal complex occurs with the time when the separated set of features associated with the first signal complex occurs.

10. The method of claim 7, wherein comparing the extracted features with a set of predetermined templates includes comparing the extracted features with a set of predetermined time versus time templates.

11. A cardiac rhythm management system, comprising:
at least one electrode;
a signal sensing circuit coupled to the electrode to sense a cardiac signal, the cardiac signal having signal complexes;
a controller coupled to the sensing circuit, wherein the controller receives the sensed cardiac signal, and wherein the controller includes:
memory configured to store at least a first signal complex; and
an analyzing module configured to:
compute curvatures at sample points of the sensed cardiac signal,
continuously process the sensed cardiac signal to produce an absolute value of the first derivative of the sensed cardiac signal, and
compare the absolute value of the first derivative to a predetermined decaying threshold value to detect a second subsequent signal complex.

12. The system of claim 11, wherein the analyzing module separates a set of features associated with the first signal complex upon detecting the second signal complex.

13. The system of claim 11, wherein the second signal complex is detected when the absolute value of the first derivative of the cardiac signal exceeds the predetermined decaying threshold value.

14. The system of claim 12, wherein the analyzer module is configured to identify a fiducial feature from the set of separated features associated with the first signal complex.

15. The system of claim 14, wherein the fiducial feature is identified based on comparing a time when the first signal complex occurs with the time when the separated features occur.

16. The system of claim 12, wherein the memory stores the features associated with the first signal complex, and the stored features are replaced with features of the second signal complex when the second signal complex is detected.

17. A method comprising:
sensing a cardiac signal using an implantable medical device;
computing curvature at sample points on the sensed cardiac signal;
computing average curvature between two adjacent sample points by computing an integral of the curvature between the two adjacent sample points;
extracting features from the computed curvatures;
comparing the extracted features with a set of predetermined templates; and
classifying the sensed cardiac signal based on an outcome of the comparison.

18. The method of claim 17, wherein computing the curvature at sample points on the sensed cardiac signal includes computing a curvature versus time curve, and wherein computing an integral of the curvature includes finding the area under a curvature versus time curve.

19. The method of claim 18, wherein extracting features from the computed curvatures includes defining the features by a value of the area under the curvature versus time curve.

20. The method of claim 19, wherein extracting features from the computed curvatures includes comparing the value of the area for the features to an area threshold value and eliminating features with area values less than the threshold area value.

* * * * *